(12) United States Patent
Zarembo (10) Patent No.: US 7,238,883 B2
(45) Date of Patent: Jul. 3, 2007

(54) LEAD ASSEMBLY WITH FLEXIBLE PORTIONS AND METHOD THEREFOR

(75) Inventor: Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 57 days.

(21) Appl. No.: 10/916,313

(22) Filed: Aug. 11, 2004

(65) Prior Publication Data

US 2006/0032657 A1    Feb. 16, 2006

(51) Int. Cl.
*A61N 1/05* (2006.01)

(52) U.S. Cl. .................. 174/69; 607/119; 607/122; 607/123

(58) Field of Classification Search ............... 174/69; 607/119, 122, 123
See application file for complete search history.

(56) References Cited

U.S. PATENT DOCUMENTS

| | | | |
|---|---|---|---|
| 3,209,305 A * | 9/1965 | Bruckner et al. ........... 439/289 |
| 3,974,834 A | 8/1976 | Kane | |
| 4,046,151 A | 9/1977 | Rose | |
| 4,307,928 A | 12/1981 | Petlock, Jr. | |
| 4,471,777 A | 9/1984 | McCorkle, Jr. | |
| 4,576,162 A | 3/1986 | McCorkle | |
| 4,582,056 A | 4/1986 | McCorkle, Jr. | |
| 4,998,975 A | 3/1991 | Cohen et al. | |
| 5,103,821 A | 4/1992 | King | |
| 5,224,491 A | 7/1993 | Mehra | |
| 5,246,014 A * | 9/1993 | Williams et al. ............ 607/122 |
| 5,336,252 A | 8/1994 | Cohen | |
| 5,342,413 A | 8/1994 | Hirschberg et al. | |
| 5,387,234 A | 2/1995 | Hirschberg | |
| 5,409,469 A | 4/1995 | Schaerf | |
| 5,411,527 A | 5/1995 | Alt | |
| 5,423,806 A | 6/1995 | Dale et al. | |
| 5,531,779 A | 7/1996 | Dahl et al. | |
| 5,639,276 A | 6/1997 | Weinstock et al. | |
| 5,649,974 A | 7/1997 | Nelson et al. | |
| 5,674,217 A | 10/1997 | Wahlstrom et al. | |
| 5,674,272 A | 10/1997 | Bush et al. | |
| 5,713,867 A | 2/1998 | Morris | |
| 5,769,858 A | 6/1998 | Pearson et al. | |
| 5,843,141 A | 12/1998 | Bischoff et al. | |
| 5,851,226 A | 12/1998 | Skubitz et al. | |
| 5,871,530 A | 2/1999 | Williams et al. | |
| 5,897,584 A | 4/1999 | Herman | |
| 5,902,331 A | 5/1999 | Bonner et al. | |
| 5,932,360 A | 8/1999 | Hazlitt et al. | |
| 5,994,444 A | 11/1999 | Trescony et al. | |
| 6,038,472 A | 3/2000 | Williams et al. | |
| 6,043,273 A | 3/2000 | Duhaylongsod | |
| 6,445,954 B1 | 9/2002 | Olive et al. | |
| 2004/0054390 A1 | 3/2004 | Zarembo et al. | |
| 2005/0228469 A1 | 10/2005 | Zarembo et al. | |

OTHER PUBLICATIONS

"Servometer Miniature Metal Bellows", http://www.servometer.com/bellows.html, Downloaded from: http://web.archive.org/web/20041016084534/http://www.servometer.com/bellows.html,(Oct. 16, 2004 (Archived Copy)) 3 pgs.

* cited by examiner

*Primary Examiner*—Jinhee Lee
(74) *Attorney, Agent, or Firm*—Schwegman, Lundberg, Woessner, & Kluth, P.A.

(57) ABSTRACT

A lead assembly includes an outer insulative body, a conductor, and at least one electrode electrically coupled with the at least one conductor. The outer insulative body extends from a proximal end to a distal end and has an intermediate portion therebetween. A flexible portion for example having a bellows portion is disposed along the lead body.

21 Claims, 5 Drawing Sheets

LEAD ASSEMBLY WITH FLEXIBLE PORTIONS AND METHOD THEREFOR

TECHNICAL FIELD

Leads for conducting electrical signals to and from the heart, and more particularly, leads including flexible portions.

TECHNICAL BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

To implant the lead within the patient, the lead is often fed intravenously toward the heart. The lead may be implanted within or travel through complex or tortuous vasculature. The lead may also need to travel through vasculature having increasingly smaller diameters. However, conventional lead designs may be ill equipped to travel into the smaller sized vessels of the vasculature, or to make the twists and bends required to get to the desired location within the patient.

There is a need for a lead having a lead body with an ability to travel through tortuous vasculature. In addition, there is a need for a lead with a lead body that has a minimal outer diameter and that minimizes trauma to the tissue.

SUMMARY

A lead assembly is provided including an outer insulative body that extends from a proximal end to a distal end. At least one conductor is disposed within the outer insulative body, and at least one electrode is electrically coupled with the at least one conductor. The lead assembly further includes a flexible portion that has a bellows portion that is disposed along the outer insulative body.

Several options for the lead assembly are as follows. For example, in one option, the bellows portion forms a hermetic seal between two or more portions of the insulative body, or the bellows portion is formed of a metal, such as a shape memory metal. In a further option, the bellows portion has an outer edge portion where the outer edge portion forms a spiral helix shape. At least one electrode includes an electrode bellows portion, in one option.

Other options for the flexible portion with the bellows portion relate to the location of the bellows portion along the lead assembly. For instance, in one option, the bellows portion is disposed at a proximal end of the outer insulative body, for example, between a connector terminal end and a portion of the lead body. In another option, the flexible portion is disposed at the distal end of the outer insulative body. The bellows portion and/or the outer insulative lead body can form a number of different shapes. For example, the bellows portion, in one option, is disposed along a helical portion of the outer insulative body.

In another embodiment, a lead assembly is provided that includes a tubular insulative body that extends from a proximal end to a distal end, and at least one conductor that is disposed within the tubular insulative body. At least one electrode is electrically coupled with the at least one conductor, where optionally the at least one electrode includes an electrode undulating portion. The lead assembly further includes an undulating portion that is disposed along the tubular insulative body. For example, in one option, the undulating portion is disposed at a proximal end of the tubular insulative body, for example, between a proximal end and a terminal connector. In another option, the undulating portion forms part of the conductor of the lead assembly.

A method is further provided that includes coupling a conductor with at least one electrode, and disposing the conductor and the least one electrode within an insulative body. The method further includes coupling a flexible bellows portion along a portion of the insulative body. Several options for the method are as follows. For instance, in one option the method of forming a flexible bellows portion includes forming a hermetic seal with the flexible bellows portion. In another option, the location of the flexible bellows portion along the insulative body can vary. For example, the flexible bellows portion can be coupled directly adjacent to the at least one electrode, or it can be disposed at the proximal end of the insulative body, or can be disposed at a distal end of the insulative body. In yet another option, the method further includes elongating the flexible bellows portion and decreasing an outer diameter of the flexible bellows portion. In yet another option, the method further includes compressing the flexible bellows portion and increasing an outer diameter of the flexible bellows portion.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
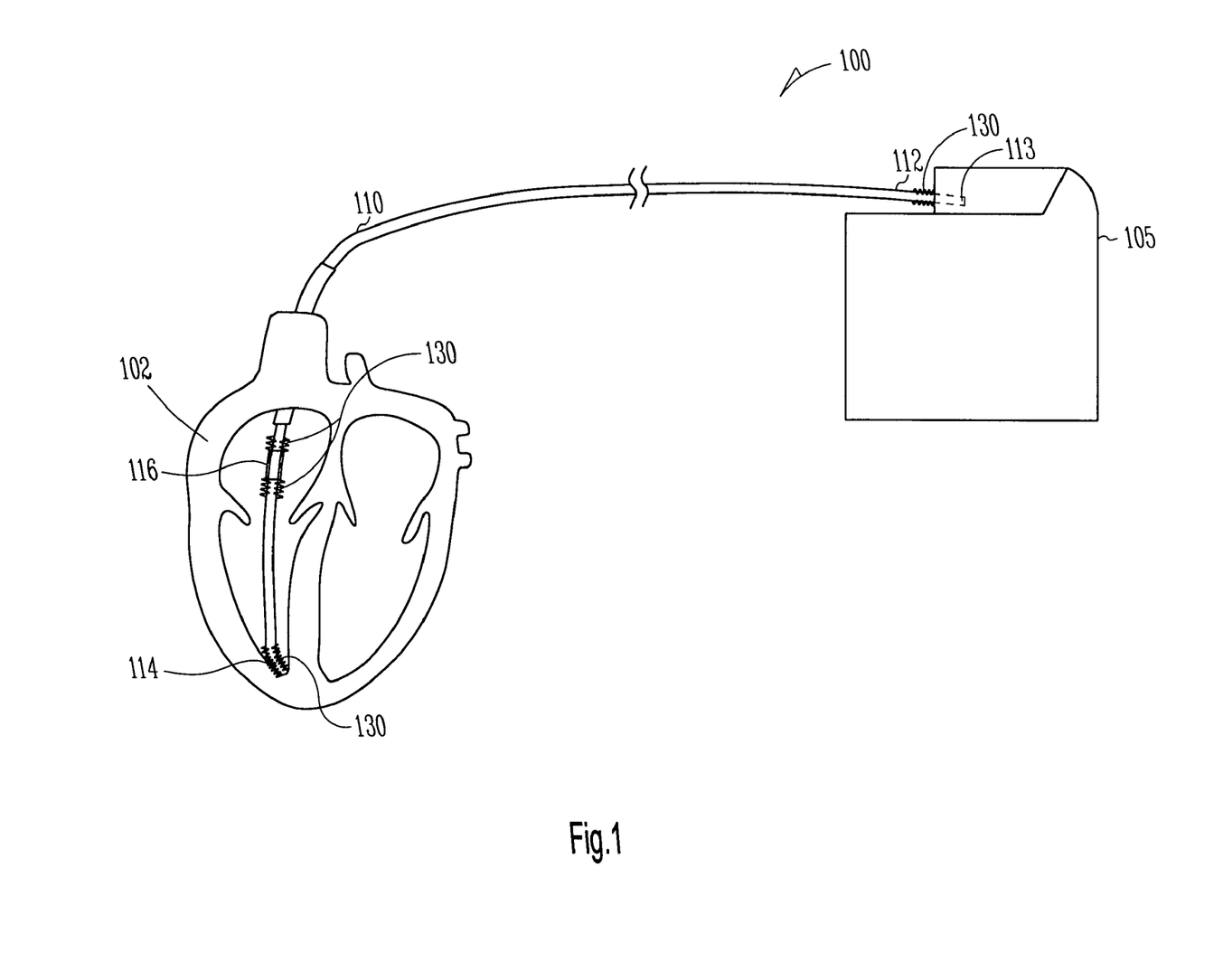
FIG. 1 illustrates a block diagram of a lead assembly constructed in accordance with one or more embodiments.

FIG. 1 illustrates an implantable device, such as a lead assembly 100 for use with an energy source such as an electrical stimulator 105. The electrical stimulator 105, in one option, is a pulse sensor and generator that contain electronics to sense various electrical signals of the heart and also produce current pulses for delivery to the heart. The pulse sensor and generator also contains electronics and software necessary to detect certain types of arrhythmias and to correct rhythm.

Figure 4A:
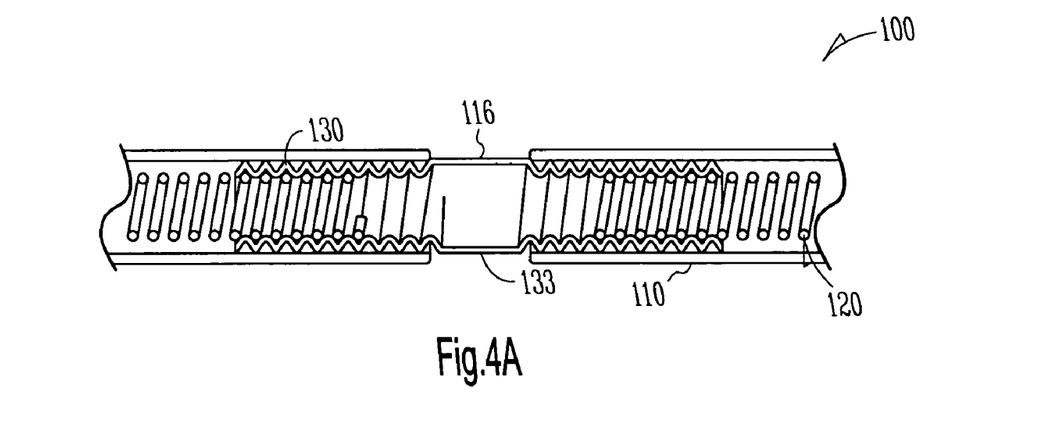
FIG. 4A illustrates a cross-sectional view of a portion of a lead assembly constructed in accordance with one or more embodiments.
Figure 4B:
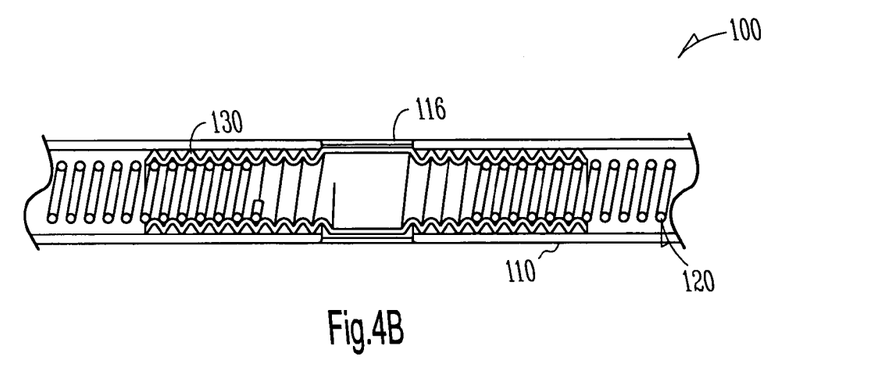
FIG. 4B illustrates a cross-sectional view of a portion of a lead assembly constructed in accordance with one or more embodiments.
Figure 4C:
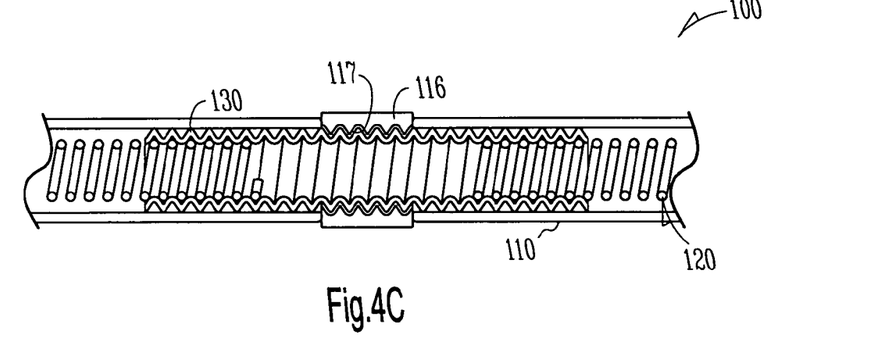
FIG. 4C illustrates a cross-sectional view of a portion of a lead assembly constructed in accordance with one or more embodiments.

The lead assembly 100 includes a lead body 110 and at least one elongate conductor 120 (FIGS. 4A–4C). The lead body 10 extends from a proximal end 112 to a distal end 114. Disposed at the proximal end 112 of the lead is a connector 113. The terminal connector 113 allows for the lead assembly 100 to be coupled with the electrical stimulator 105. The distal end of the lead 114 is disposed along, or disposed within, a portion of the heart 102. The lead assembly 100 further includes at least one electrode 116 disposed there along. The at least one electrode 116 allows for electrical signals to be delivered and/or received from the heart 102 and communicated with the energy source, such as the electrical stimulator.

The lead assembly 100 further includes one or more flexible portions 130 disposed there along. In one option, at least one flexible portion 130 is disposed at a proximal end 112 of the lead assembly 100. In one option, the flexible portion 130 is disposed between the proximal end 112 and the terminal connector 113. This allows for the flexible portion to minimize kinking where different tubing or components are used. The flexible portion 130 further allows for a strain relief between the lead assembly 100 and the energy source. The flexible portion 130, as further discussed below, allows for additional coupling options for coupling the terminal connector 113 with the remaining portions of the lead assembly 100.

Figure 3:
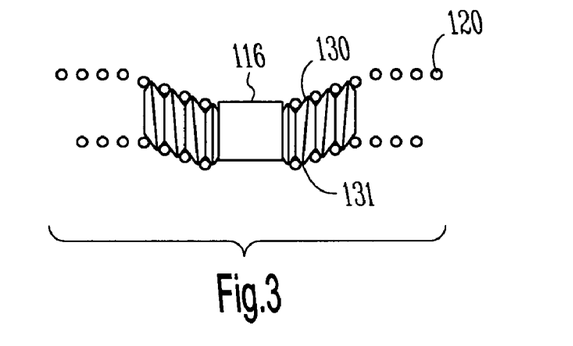
FIG. 3 illustrates an elevational view of a portion of a lead assembly constructed in accordance with one or more embodiments.

In another option, one or more flexible portions 130 are disposed along the lead body 110, for example, along an intermediate portion of the lead body 110 (see for example FIG. 3). In one option, the one or more flexible portions 130 are disposed between two tubing sections of the lead body 110. In yet another option, the one or more flexible portions 130 extend along most or the entire lead body, or along only portions of the lead body, or along segments of the lead body. For example, the one or more flexible portions extend from the distal end to an intermediate portion, and terminate for example, near an electrode. In yet another option, the flexible portion is location on the lead along a portion where the lead passes the clavicle and first rib area to prevent crushing or kinking of the lead.

In another option, the one or more flexible portions 130 are disposed directly adjacent to the electrode 116. In a further option, one or more flexible portions 130 are disposed at a distal end 114 of the lead assembly 100, for example, only at the distal end 114 of the lead assembly 100. This allows for the lead assembly 100 to remain highly flexible and/or kink and/or crush resistant near the distal end of the lead assembly 100 without disrupting any of the features along the intermediate portion.

The one or more flexible portions 130 are formed of material that is flexible, and in an option, is conductive. Extending the flexible portion 130 along the lead assembly 100, the flexible portion 130 can serve as the conductor for the lead assembly 100 in an option, and as further described below. This allows for the conductor to be hermetically sealed along its longitudinal axis, and can be made smaller than conventional conductor designs.

Figure 2:
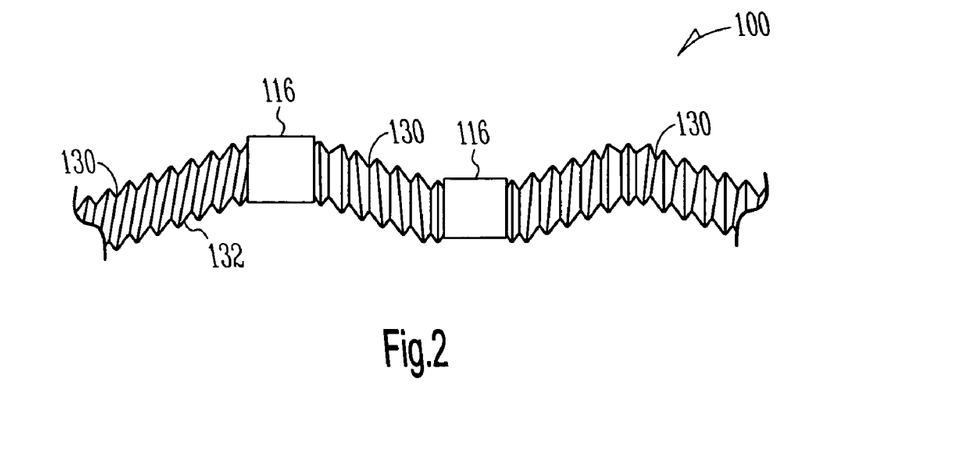
FIG. 2 illustrates an elevational view of a portion of a lead assembly constructed in accordance with one or more embodiments.

FIG. 2 illustrates one embodiment of the lead assembly 100. The one or more flexible portions 130, in one option, form the lead body along the length of the lead assembly 100. In one option, the one or more flexible portions 130 extend between at least a first electrode 116 and a second electrode 116. This is advantageous as commonly the electrode is a weak link in axial strength, sealing, and tube bonding. Some of the features on the ends of the electrode will bond to the flexible portions. This further allows for the lead assembly 100 to traverse tortuous paths of the human vasculature.

FIG. 3 illustrates another option where the one or more flexible portions 130 are disposed adjacent to the electrode 116. In an option, the one or more flexible portions 130 and the electrode 116 form a subassembly, where the electrode 116 may or may not be integrally formed with the one or more flexible portions 130. The subassembly can include coupling portions 131, where the conductor 120 can be coupled therewith. The conductors 120 can be coupled with an outer portion of the one or more portions 130, as illustrated in FIG. 3, or with an inner portion of the one or more portions 130, as illustrated in FIG. 4A. The conductor 120 can be coupled with the flexible portions 130 in a number of manners, including, but not limited to a compression fit, weld, swage, or crimp.

The subassembly, including the electrode 116, includes flexible portions on either or both ends of the electrode 116. The lead body 110 is disposed over a portion of the subassembly allowing for the electrode 116 to be exposed. The exposed surface area of the electrode 116 can be modified, see for example FIG. 4A and FIG. 5, to vary the amount of exposed surface area.

Figure 5:
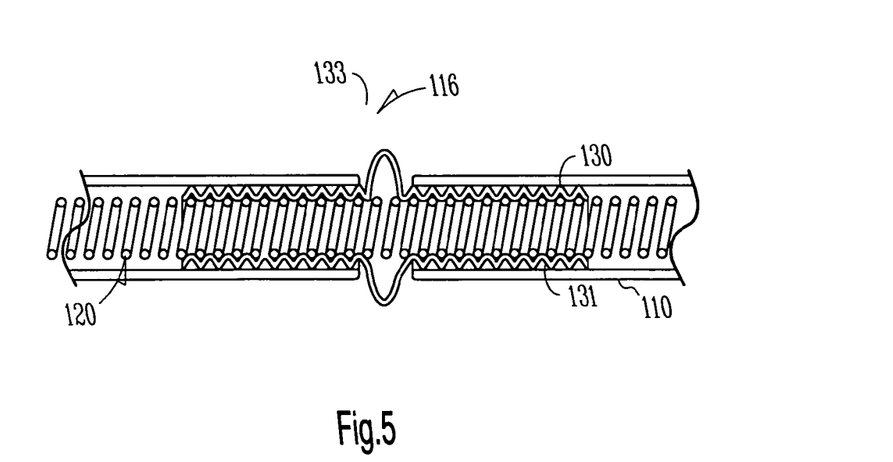
FIG. 5 illustrates a cross-sectional view of a portion of a lead assembly constructed in accordance with one or more embodiments.

FIGS. 4A–4C illustrate further options for the flexible portion 130. In one option, the portion flexible portion 130 extends from under a portion of the lead body 110, to an exposed portion 133, and optionally again extends under the lead body 110. The exposed portion 133, optionally formed integrally with the flexible portion 130, forms the electrode 116 of the lead assembly. The exposed portion 133 can have a non-planar and/or flexible cross-section, for example, as illustrated in FIG. 5. In another option, the exposed portion 133 can have a substantially planar cross-section, such as similar to a ring electrode, as illustrated in FIG. 4A.

The electrode 116, in a further option, can be formed integrally as discussed above, or can be formed separately and coupled with a portion of the flexible portion 130. For example, the electrode 116 can optionally include coupling features 117 such as threads which are threadingly coupled with the flexible portion 130, as illustrated in FIG. 4C. The coupling features 117 can be formed as helical features such as threads, or have other cross-sections which allow for the coupling features 117 to mate with the undulating portion, as discussed below.

Figure 6:
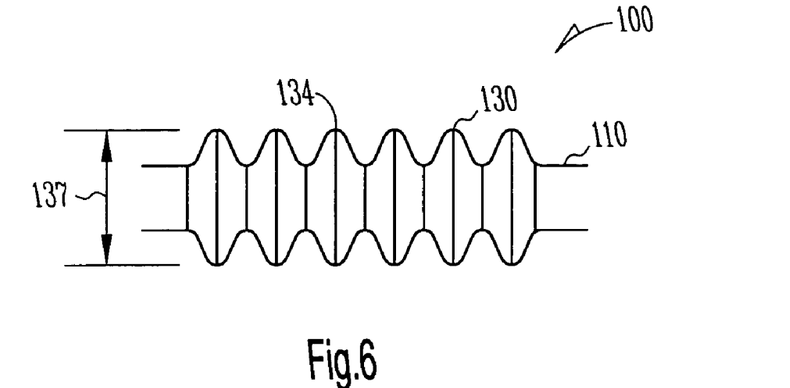
FIG. 6 illustrates an elevational view of a portion of a lead assembly constructed in accordance with one or more embodiments.
Figure 7:
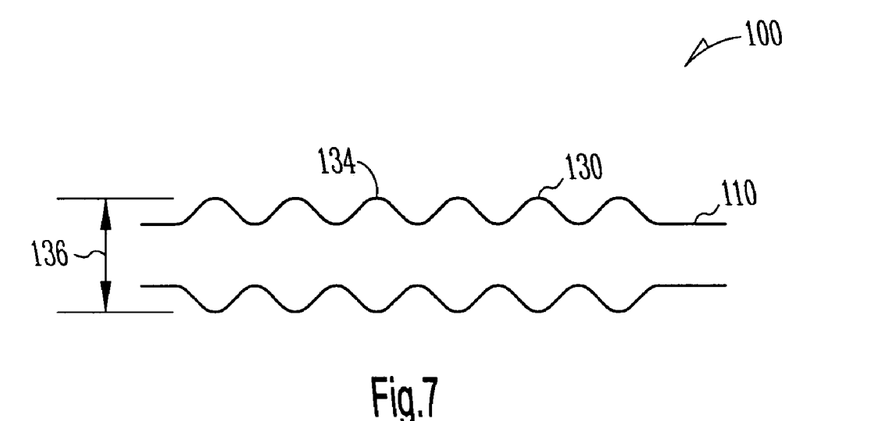
FIG. 7 illustrates an elevational view of an elongated portion of a lead assembly constructed in accordance with one or more embodiments.

FIGS. 6–9 illustrate additional variations for the one or more flexible portions 130. FIGS. 6 and 7 illustrate examples of a flexible portion 130 disposed along the lead body 110 that includes an undulating portion 134. The undulating portion 134 includes, for example, a series of wave or wave-like structures disposed along the lead body 110 that allows for the flexible portion 130 to remain flexible. The undulating portion 134 can be made from a number of materials, for example, including conductive material.

It should be noted that the undulating portions 134 can be disposed along other portions of the lead assembly 100, as further discussed above. Furthermore, other profiles for the undulating portion 134 can be used as well. For example, the undulating portion can have, but are not limited to, square shaped, V-shaped, modified square shaped, or modified buttress shaped profiles, where the profiles can be disposed in a spiral, or non-spiral configuration. The pitch of the undulating portion can be varied to arrive at different stiffnesses or to mate with coil pitches. Furthermore, the outer diameter of the undulating portion 134 can be varied longitudinally along the lead assembly, where the outer diameter varies dimensionally prior to manipulation such as elongation or compression of the undulating portion 134.

In one option, the flexible portion 130, such as the undulating portion 134, is defined by an outer dimension in both a stretched or unstretched position. For example, the undulating portion 134 is defined by an outer dimension 137 in an unstretched position as illustrated in FIG. 6. The undulating portion 134 is further defined by an outer diameter 136 when the flexible portion 130 is in an elongated or stretched position, as illustrated in FIG. 7. As illustrated in the drawings of FIG. 6 and FIG. 7, the outer dimensions 137 and 136 differ in that the outer dimension decreases as the flexible portion is elongated. For example, as a lead is explanted from the vasculature, the outer diameter can be reduced through use of the flexible portions 130, thereby facilitating explantation of the lead from the patient. Alternatively, a sheath, stylet, or catheter can be used to reduce the outer diameter of the flexible portion, and then removed when the electrode or the flexible portion 130 is in position within the heart or vasculature.

Figure 8:
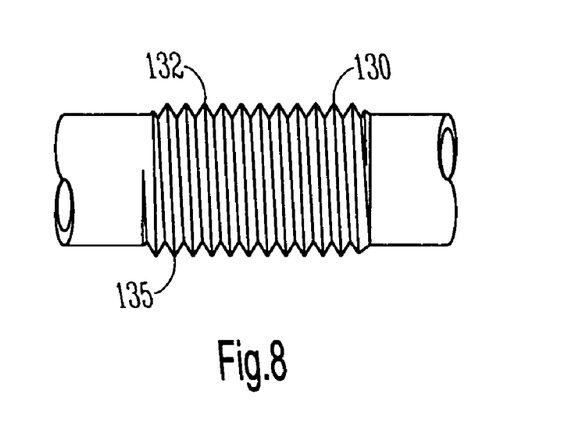
FIG. 8 illustrates an elevational view of a portion of a lead assembly constructed in accordance with one or more embodiments.
Figure 9:
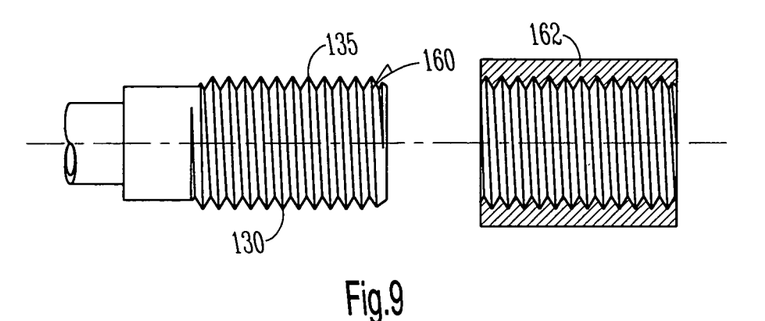
FIG. 9 illustrates an elevational view of a proximal portion of a lead assembly constructed in accordance with one or more embodiments.

In another option, the flexible portion 130 includes a series of features that are elongatable, however, have an outer structure that is similar to a helical structure, as illustrated in FIG. 8. The helical portion 135 allows for the coils to be coupled to the flexible portion 130, for example, by threading the coils with the helical portion 135. In addition, the helical portion 135, which can be located in a variety of locations along the lead, can allow for other components to be threadingly coupled therewith. For example, a terminal end 160 (FIG. 9) of the lead provided with a helical portion 135 discussed above can be coupled, i.e. by threading, with a connector 162 (FIG. 9), or a portion of a pulse generator that includes mating features, where the helical structure can be disposed on an inner portion of the mating part, an outer portion of the mating part, or a combination of both. Such helical mating features can be disposed along other locations of the lead assembly, including, but not limited to the electrode subassembly discussed above. The helical features can also mate with other components, such as, coil filars of the conductor, threaded electronics, or lead fixation components.

The one or more flexible portions 130 include a flexible bellows portion 132 (FIG. 2). In another option, the flexible portions 130 include an undulating portion 134 disposed along the insulative body 110, where optionally the flexible portions 130 are formed of at least in part insulative material.

In another option, the one or more flexible portions 130 are formed of electrically conductive material. For example, the flexible portion can be formed from one or more metals including, but not limited to, nitinol, Pt, Ti, PtIr. These materials can form base metals, and in one option, subsequently coated with other metals or oxides to provide optimal pacing or sensing characteristics for electrodes. Alternatively, the flexible bellows portion can be formed of a polymer, or a material coated with insulative material, such as parylene coated metal. It should be noted that the insulative coating can be a partial coating, or can completely cover the flexible bellows portion. In yet another option, the flexible bellows portion can be formed of shape memory material that can be activated into a predetermined shape by, for example, heat or current passed to the bellows resulting in heat.

In one option, the flexible portion is formed by plating a material over a dissolvable mandrel, and then removing the mandrel, for example, by etching it away. In one example, copper and/or nickel is plated over aluminum mandrel, and then the aluminum mandrel is etched away. The materials that are coated over the mandrel or base material can be done so by plating, sputtering, and/or vapor deposition. These procedures, among others, allow for the flexible portion to be made highly flexible, and also have a high fatigue resistance. It also allows for the wall thickness to be made quite thin. For example, the wall thickness can be made, in an option, about 0.0005 to 0.005 inches in thickness. Furthermore, even though the material is thin and quite flexible, the material or the flexible portion can be made to have a hermetic seal between the tubing sections or as an electrode, as further described below.

Figure 10:
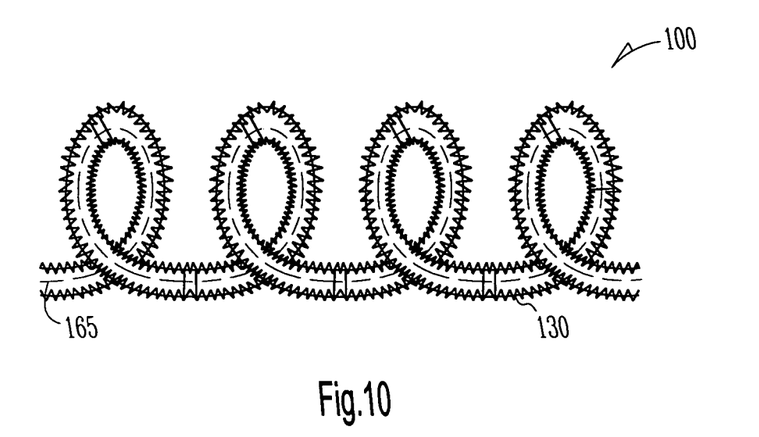
FIG. 10 illustrates an elevational view of a portion of a lead assembly constructed in accordance with one or more embodiments.
Figure 11:
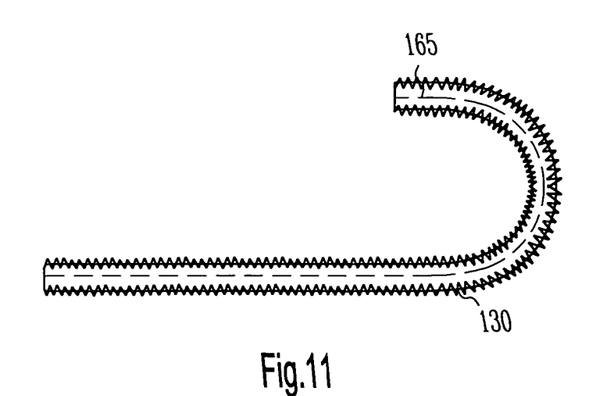
FIG. 11 illustrates an elevational view of a portion of a lead assembly constructed in accordance with one or more embodiments.

FIGS. 10 and 11 illustrate additional options for the lead assembly, where the lead assembly includes one or more flexible portions 130. The one or more flexible portions includes the options discussed above, such as, but not limited to, the undulating portions, and the flexible bellows portions. In an option, the lead assembly is defined in part by a longitudinal axis 165. The longitudinal axis of the assembly is formed into a three-dimensional shape, such as a helical shape, as illustrated in FIG. 10, where optionally the one or more flexible portions 130 are disposed therealong, and optionally form part of the electrode. The electrode, having the helical shape, and the flexible portion features (i.e. the flexible bellows portion, the undulating portion), allows it to be disposed against interior surfaces of the human vasculature, or cardiac chambers or structures for lead fixation or intimate contact with myocardial cells. For example, the flexible portion 130 can be disposed against an inner wall of a vein, artery or heart chamber. In another option, the longitudinal axis 165 of the lead assembly is formed into a two-dimensional shape, such as a J-shape, as illustrated in FIG. 11, and one or more of the flexible portions 130 are disposed therealong. It should be noted that other shapes can be formed to aid in lead fixation or navigation such as sinusoidal, canted, or other two or three dimensional shapes, and can be preformed into the lead assembly.

A method further is provided herein that includes coupling a conductor with at least one electrode, and disposing the conductor and the least one electrode within an insulative body. The method further includes coupling a flexible bellows portion along a portion of the insulative body, for example, along a proximal or intermediate portion of the insulative body.

Several options for the method are as follows. In another option, the location of the flexible bellows portion along the insulative body can vary. For example, the flexible bellows portion can be coupled directly adjacent to the at least one electrode, or it can be disposed at the proximal end of the insulative body, or can be disposed at a distal end of the insulative body. In yet another option, the method further includes elongating the flexible bellows portion and decreasing an outer diameter of the flexible bellows portion. In yet another option, the method further includes compressing the flexible bellows portion and increasing an outer diameter of the flexible bellows portion, for example, for fixating a portion of the lead assembly. The method of forming a flexible bellows portion optionally includes forming a hermetic seal with the flexible bellows portion.

Advantageously, the flexible portions of the lead assembly 100 allows for a lead that is more maneuverable within the patient's vasculature than, for example, previous rigid cylindrical electrodes or other components that are relatively more rigid. Furthermore, the flexible portion allows for a hermetic seal to be formed in places where previously it was impossible. For example, in places where a coil conductor was used. Furthermore, the flexible portions allow for portions of the lead assembly to be reduced in outer diameter, for example, during explantation or implantation within a patient. This allows for further ease of navigation throughout the vasculature. The flexible portion design, for example within use as the electrode, allows for use of a longer electrode with a higher surface area.

It is to be understood that above description is intended to be illustrative, and not restrictive. Although the use of the implantable device has been described for use as a lead in, for example, a cardiac stimulation system, the implantable device could as well be applied to other types of body stimulating systems. Furthermore, it should be noted that the embodiments, and various options described above and illustrated in the drawings, may be selectively combined to form additional embodiments. Many other embodiments will be apparent to those of skill in the art upon reviewing the above description. The scope should, therefore, be determined with reference to the appended claims, along with the full scope of equivalents to which such claims are entitled.

What is claimed is:

1. A lead assembly comprising:
an outer insulative body extending from a proximal end to a distal end, and having an intermediate portion therebetween;
at least one conductor disposed within the outer insulative body;
at least one tissue stimulating electrode electrically coupled with the at least one conductor;
and
a flexible portion having a bellows portion disposed along at least a portion of the outer insulative body, wherein the flexible portion is fixed with respect to at least one of the outer insulative body, the conductor, or the tissue stimulating electrode.

2. The lead assembly as recited in claim 1, wherein the bellows portion forms a hermetic seal between two portions of the insulative body.

3. The lead assembly as recited in claim 1, wherein at least a portion of the bellows portion is formed of at least one of a metal or a polymer.

4. The lead assembly as recited in claim 1, wherein the bellows portion forms a spiral helix.

5. The lead assembly as recited in claim 4, wherein a component is threadingly coupled with the spiral helix of the bellows portion.

6. The lead assembly as recited in claim 5, wherein the component is the conductor.

7. The lead assembly as recited in claim 5, wherein the component is a connector terminal.

8. The lead assembly as recited in claim 1, wherein the bellows portion forms a strain relief at the proximal end.

9. The lead assembly as recited in claim 1, wherein the at least one electrode includes an electrode bellows portion.

10. The lead assembly as recited in claim 1, wherein the flexible portion having the bellows portion is disposed at the proximal end of the outer insulative body.

11. The lead assembly as recited in claim 10, further comprising a terminal end, where the bellows portion is disposed between the proximal end and the terminal end.

12. The lead assembly as recited in claim 1, wherein outer insulative body is defined in part by a longitudinal axis and the longitudinal axis has a two or three dimensional shape, and the bellows portions is disposed along the two or three dimensional shape.

13. The lead assembly as recited in claim 1, wherein the flexible bellows portion has a relatively decreased outer diameter when the flexible bellows portion has an elongated configuration.

14. A lead assembly comprising:
an intravenously implantable tubular insulative body extending from a proximal end to a distal end;
at least one conductor disposed within the tubular insulative body;
at least one electrode electrically coupled with the at least one conductor;
and
an electrically conductive undulating portion disposed along the tubular insulative body, wherein the electrically conductive undulating portion is fixed with respect to at least one of the intravenously implantable tubular insulative body, the conductor, or the electrode.

15. The lead assembly as recited in claim 14, wherein the undulating portion is disposed at the distal end of the tubular insulative body.

16. The lead assembly as recited in claim 14, wherein the undulating portion is formed of metal.

17. The lead assembly as recited in claim 14, wherein the at least one electrode includes an electrode undulating portion.

18. The least assembly as recited in claim 17, wherein the undulating portion is threadingly coupled with the at least one electrode.

19. The lead assembly as recited in claim 14, wherein the flexible portion having the undulating portion is disposed at the proximal end of the tubular insulative body.

20. The lead assembly as recited in claim 19, further comprising a terminal connector, where the undulating portion is disposed between the proximal end and the terminal connector.

21. The lead assembly as recited in claim 14, wherein the undulating portion forms a strain relief at the proximal end.

* * * * *

UNITED STATES PATENT AND TRADEMARK OFFICE
CERTIFICATE OF CORRECTION

PATENT NO. : 7,238,883 B2  Page 1 of 1
APPLICATION NO. : 10/916313
DATED : July 3, 2007
INVENTOR(S) : Zarembo It is certified that error appears in the above-identified patent and that said Letters Patent is hereby corrected as shown below:

In column 8, line 62, in Claim 18, delete "least" and insert -- lead --, therefor.

Signed and Sealed this

Eleventh Day of September, 2007

JON W. DUDAS
*Director of the United States Patent and Trademark Office*